US00RE38484E

(19) United States
(12) Reissued Patent
Nakamura et al.

(10) Patent Number: US RE38,484 E
(45) Date of Reissued Patent: Mar. 30, 2004

(54) CATIONIZED HYDROXYALKYLCELLULOSE AND PROCESS FOR PRODUCING THE SAME

(75) Inventors: Hiroyuki Nakamura, Hyogo (JP); Shigenobu Sato, Hyogo (JP)

(73) Assignee: Daicel Chemical Industries, Ltd., Osaka (JP)

(21) Appl. No.: 10/120,341

(22) Filed: Apr. 11, 2002

Related U.S. Patent Documents

Reissue of:
(64) Patent No.: 6,197,950
Issued: Mar. 6, 2001
Appl. No.: 09/246,247
Filed: Feb. 8, 1999

(30) Foreign Application Priority Data

Jul. 7, 1998 (JP) ..... 10-191404

(51) Int. Cl.[7] ..... C08B 1/00; C08B 3/00; C08B 11/00; C08B 15/00

(52) U.S. Cl. ..... 536/30; 536/31; 536/32; 536/56; 536/58; 536/123.1; 536/124

(58) Field of Search ..... 536/30, 31, 32, 536/33, 34, 36, 37, 41, 42, 56, 58, 124, 123.1

(56) References Cited

FOREIGN PATENT DOCUMENTS

| | | | |
|---|---|---|---|
| EP | 0 189 935 | * | 1/1986 |
| JP | 45-20318 | * | 7/1970 |
| JP | 53-090368 | * | 8/1978 |
| JP | 59-42681 | * | 10/1984 |
| JP | 62-132901 | * | 6/1987 |
| JP | 63-072701 | * | 4/1988 |

* cited by examiner

*Primary Examiner*—James O. Wilson
*Assistant Examiner*—Patrick K Lewis
(74) *Attorney, Agent, or Firm*—Flynn, Thiel, Boutell & Tanis, P.C.

(57) ABSTRACT

Cationized hydroxyalkylcelluloses, which are highly compatible with surfactants, are represented by the following formula (I):

(I)

wherein $R^1$, $R^2$ and $R^3$ represent a hydrogen atom or a group represented by the formula $CH_2CH_2OCH_2CH(OH)CH_2N^+(CH_3)Cl^-$, etc.; and "n" is a number of from 50 to 2,000; which have a mobility distribution (ΔU) determined by electrophoresis ranging from $0.1\times[10^5]10^{-5}$ to $2.0\times[10^5]10^{-5}$ $cm^2sec\cdot V$.

7 Claims, 1 Drawing Sheet

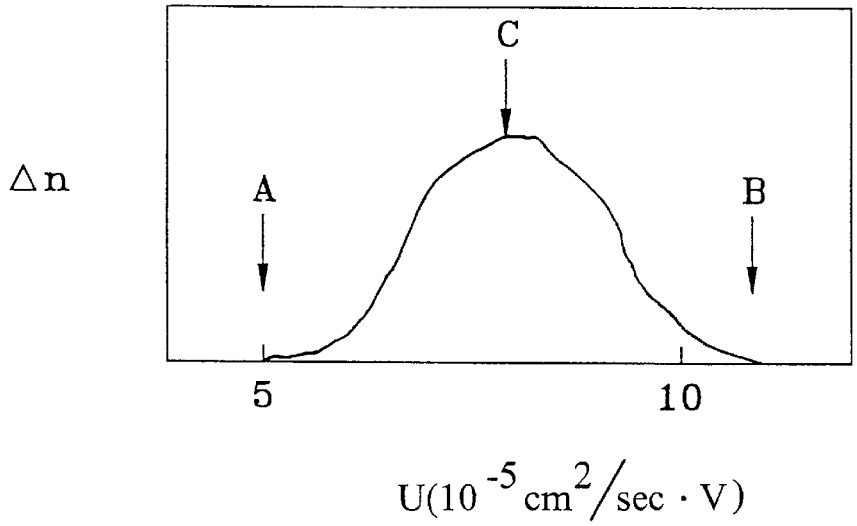
FIG. 1 (AMENDED)
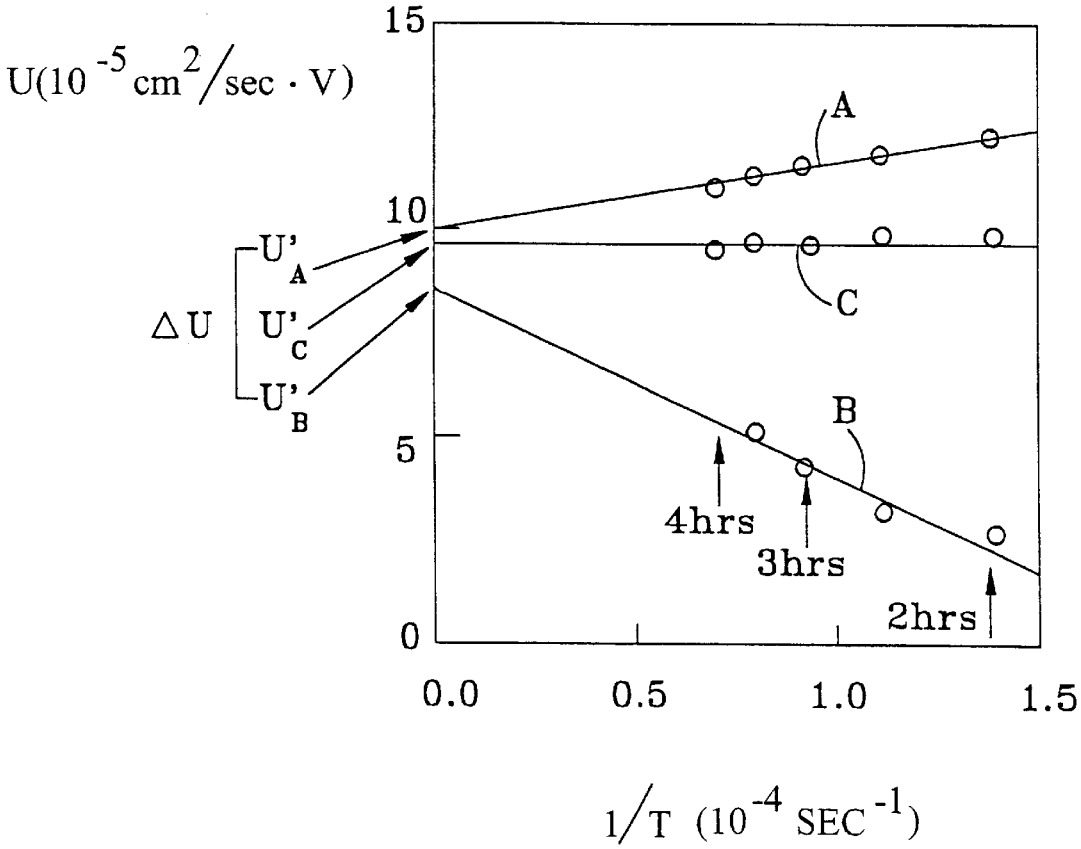
FIG. 2 (AMENDED)

CATIONIZED HYDROXYALKYLCELLULOSE AND PROCESS FOR PRODUCING THE SAME

Matter enclosed in heavy brackets [ ] appears in the original patent but forms no part of this reissue specification; matter printed in italics indicates the additions made by reissue.

*This application is a reissue application of U.S. Ser. No. 09/246 247, filed Feb. 8, 1999, now U.S. Pat. No. 6,197,950, issued on Mar. 6, 2001.*

BACKGROUND OF THE INVENTION

1. Field of the Invention

The present invention relates to cationized hydroxyalkylcelluloses which are useful as components of shampoos, rinses, treatments, etc. and a process for producing the same.

2. Prior Art

Cationized hydroxyalkylcelluloses are known as components of shampoos, rinses, treatments, etc., since they contain quaternary ammonium groups as substituents. When employed as components of shampoos, rinses, treatments, etc., these cationized hydroxyalkylcelluloses should be highly compatible with surfactants which are employed as the principal components therein.

As a process for the production of cationized hydroxyalkylcelluloses, JP-B 45-20318 has disclosed a process comprising using cellulose as the starting material, adding an etherifying agent and a cationizing agent successively or simultaneously thereto and thus effecting a continuous reaction. However, this process is not advantageous economically, since the etherifying agent and the cationizing agent are each utilized only at a poor efficiency. Moreover, there arises another problem that it is highly troublesome to eliminate the unreacted materials and impurities formed in large amounts as by-products.

Meanwhile, JP-B 59-42681 has disclosed a process with the use of an ethylene oxide derivative or a propylene oxide derivative of cellulose as the starting material. Although a cationizing agent can be utilized at a high efficiency in this process, it is necessary in this process to react and wash again a cellulose ether which has once reacted and washed, i.e., the reaction and washing should be performed twice. In this process, a solvent mixture of isopropanol with water is used as a reaction solvent in most cases. When, however, the obtained product has a high degree of hydroxylalkyl-substitution, it is dissolved in the above reaction solvent. As a result, it becomes difficult to stir the reaction system due to the increased viscosity, which brings about a decrease in the conversion.

Further, in the prior art, there has not been developed so far any process by which the above-mentioned problems can be solved and cationized hydroxyalkylcelluloses having a high compatibility with surfactants can be constantly supplied.

DISCLOSURE OF THE INVENTION

An object of the present invention is to provide cationized hydroxyalkylcelluloses which are highly compatible with surfactants and useful as components of hair care products such as shampoos.

Another object of the present invention is to provide a process for producing these cationized hydroxyalkylcelluloses.

The present invention provides a cationized hydroxyalkylcellulose having a glucose unit represented by the following formula (I):

(I)

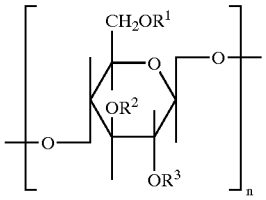

wherein $R^1$, $R^2$ and $R^3$ represent hydrogen atom, a group represented by the following formula (II):

(II)

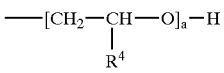

wherein $R^4$ represents hydrogen atom or methyl; and "a" is a number of from 1 to 6 on the average, or represented by the following formula (III):

(III)

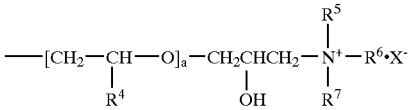

wherein $R^4$ represents hydrogen atom or methyl; "a" is a number of from 1 to 6 on the average; $R^5$, $R^6$ and $R^7$ are the same as or different from each other and represent a $C_{1-16}$ alkyl; X represents a halogen; and "n" is a number of from 50 to 2,000, the cationized hydroxyalkyl cellulose having a mobility distribution (ΔU), determined by electrophoresis, in the range of from $0.1\times[10^5]10^{-5}$ to $2.0\times[10^5]10^{-5}$ $cm^2/sec\cdot V$, including the above shown group (III) to have a nitrogen atom content (%) of from 0.1 to 10. 0.

The present invention further provides a process for producing a cationized hydroxyalkylcellulose, comprising the steps of mixing a hydroxyalkylcellulose with an aqueous solution of isopropyl alcohol or an aqueous solution of t-butyl alcohol; adding an alkali to the mixture; effecting cationization; and effecting neutralization.

DETAILED DESCRIPTION OF THE INVENTION

The cationized hydroxyalkylcellulose of the present invention is one represented by the formula (I) wherein $R^1$, $R^2$ and $R^3$ represent hydrogen, a group represented by the formula (II) or another group represented by the formula (III).

It is preferable that the substituent represented by the formula (II) has an average degree of substitution per glucose unit ranging from 0.4 to 2.9 and an average mole number ranging from 1.0 to 7.0. It is still preferable that the substituent represented by the formula (II) has an average degree of substitution per glucose unit ranging from 0.7 to 2.1 and an average mole number ranging from 1.6 to 3.6.

Although the upper limit of "a" in the substituent represented by the formula (II) is not specified theoretically, it is preferable that "a" ranges from 1 to 6 on the average.

The substituent represented by the formula (III) has an average degree of substitution per glucose unit ranging from 0.1 to 3.0, preferably from 0.1 to 1.5 and still preferably from 0.1 to 0.9.

Although the upper limit of "a" in the substituent represented by the formula (III) is not specified theoretically, it is preferable that "a" ranges from 1 to 6 on the average.

In the substituent represented by the formula (III), $R^5$, $R^6$ and $R^7$ are the same as or different from each other and represent a $C_{1-6}$ alkyl, preferably methyl or ethyl.

In the formula (I), "n" represents a number of from 50 to 2,000, preferably from 50 to 1,500. Examples of the halogen represented by X in the formula (I) include chlorine, bromine and iodine.

The cationized hydroxyalkylcellulose represented by the formula (I) has a mobility distribution (ΔU) determined by electrophoresis of from $0.1\times[10^5]10^{-5}$ to $2.0\times[10^5]10^{-5}$ $cm^2/sec\cdot V$, preferably from $0.1\times[10^5]10^{-5}$ to $1.5\times[10^5]10^{-5}$ $cm^2/sec\cdot V$. By regulating ΔU to be within the range as specified above, the compatibility, of the hydroxyalkylcellulose with surfactants can be elevated.

It is preferable that the cationized hydroxyalkylcellulose represented by the formula (I) has a nitrogen atom content (%) of from 0.1 to 10.0, still preferably from 0.5 to 4.0.

It is preferable that the cationized hydroxyalkylcellulose represented by the formula (I) has a degree of substitution a quaternary nitrogen-containing grout) of from 0.1 to 1.5, still preferably from 0.1 to 0.9.

Moreover, it is preferable that the cationized hydroxyalkylcellulose represented by the formula (I) has a viscosity at 25° C. of from 30 mPa·s (as a 2%, by weight aqueous solution; 30 rpm) to 5,000 mPa·s (as a 1% by weight aqueous solution; 30 rpm), still preferably from 70 mPa·s (as a 2% by weight aqueous solution; 30 rpm) to 2,500 mPa·s (as a 1% by weight aqueous solution; 30 rpm).

Next, the process for producing the cationized hydroxyalkylcellulose of the present invention will be illustrated. Since the production process of the present invention is characterized by the type and concentration, of an organic solvent solution employed in the reaction, it is not particularly restricted in other treating procedures and conditions. That is, the present invention also involves in its scope any usual modification made by those skilled in the art in producing cationized hydroxyalkylcelluloses.

In the first step, a hydroxyalkylcellulose is mixed with an aqueous solution of isopropyl alcohol or an aqueous solution of t-butyl alcohol.

The hydroxyalkylcellulose to be used in this step can be obtained by a conventional method comprising, for example, treating cellulose with an alkali and then adding an alkylene oxide thereto. As the cellulose employed a the starting material use may be made of cotton linters, wood pulp, etc.

As the aqueous solution of isopropyl alcohol, it is preferable to use one having an isopropyl alcohol concentration of from 75 to 90% by weight, still preferably from 80 to 90% by weight. As the aqueous solution of t-butyl alcohol, it is preferable to use one having a t-butyl alcohol concentration of from 70 to 85% by weight, still preferably from 75 to 85% by weight.

It is preferable that the aqueous solution of isopropyl alcohol or the aqueous solution of t-butyl alcohol is employed in an amount of from 300 to 900 parts by weight per 100 parts by weight of hydroxyalkylcellulose.

In the second step, an aqueous solution of an alkali serving as a catalyst is added thereto. Examples of the aqueous solution of an alkali include aqueous solutions of sodium hydroxide and potassium hydroxide.

It is preferable that the alkali is used in an amount of from 0.05 to 0.4 times by mole as much as the glucose unit in the hydroxyalkylcellulose.

In the third step, cationization is effected by adding a cationizing agent. Examples of the cationizing agent to be used in this step include glycidyltrialkylammonium halides such as glycidyltrimethylammonium chloride, glycidyltriethylammonium chloride and glycidyltrimethylammonium bromide.

It is preferable that the cationizing agent is used in an amount of from 0.2 to 2.0 times by mole as much as the glucose unit in the hydroxyalkylcellulose.

In the subsequent fourth step, hydrochloric acid, sulfuric acid, etc. is added to thereby neutralize the alkali added in the above third step.

If necessary, the reaction product is purified by appropriate procedures, for example, washing with an organic solvent such as isopropyl alcohol or acetone and dried to give the cationized hydroxyalkylcellulose of the present invention.

The cationized hydroxyalkylcellulose of the present invention are useful as components of shampoos, rinses, treatments, etc.

BRIEF DESCRIPTION OF THE DRAWINGS

FIG. 1 is a diagram showing the relationship between change in refractive index (Δn) and mobility (U).

FIG. 2 is a diagram showing the relationship between mobility (U) and time (1/t).

EXAMPLES

To further illustrate the present invention in greater detail, and not by way of limitation, the following Examples will be given.

Example 1

145 g of a hydroxyethylcellulose powder containing hydroxyethylcellulose (number of moles of ethylene oxide added per anhydrous glucose unit: 2.2, viscosity of 2% by weight aqueous solution at 25° C.: 920 mPa·s) was fed into a four-necked flask provided with a condenser. Further, 1,110 g of an 89% by weight aqueous solution of isopropyl alcohol (IPA) was added and hydroxyethylcellulose was dispersed therein by stirring to give a slurry.

To this slurry was added, under stirring, 60 g of a 20% by weight aqueous solution of sodium hydroxide and the mixture was stirred at 25° C. for 120 minutes, thus effecting an alkali-treatment.

Subsequently, 100 g of a 75% by weight aqueous solution of glycidyltrimethylammonium chloride was added as a cationizing agent to the slurry and the resultant mixture was stored for 60 minutes. Then it was heated to 40° C. and stored for additional 3 hours at this temperature.

Next, the mixture was cooled to room temperature and 55 g of a 20% by weight aqueous solution of hydrochloric acid was added thereto to thereby neutralize the mixture. After stirring, the slurry was filtered. The filtration residue was added to 2,200 ml of a 76% by weight aqueous solution of acetone and the resultant mixture was stirred, washed and filtered. Subsequently, the residue was waned with a 76% by weight aqueous solution of acetone thrice and then added to 2,200 ml of a 98% by weight aqueous solution of acetone. After mixing by stirring and filtering again, the residue was dried at 70° C. for 2 hours to give 175 g of cationized hydroxyalkylcellulose.

The cationized hydroxyethylcellulose thus obtained was subjected to the measurements of the following items. Table 2 summarizes the results.

(1) Nitrogen content

Nitrogen content was determined by the quantitative method described in "Keshohin Shubetsu Haigo Seibun Kikaku (Standards for components of Cosmetic goods)", 1st ed. Apr. 18, 1997, published by K.K. Yakuji Nippo, pages 210–213, authored by the Welfare Ministry of Japan. The procedure will be described in detail.

Weigh accurately about 1.0 g of Quaternium 19, previously dried at 110° C. for 2 hours, and dissolved in water to make exactly 1,000 ml. To exactly 5 ml of this solution add water to make 50 ml, add 4 drops of a toluidine blue solution (1→1,000), then titrate with 0.0025 N potassium polyvinyl sulfate. Perform a blank determination in the same manner, and make any necessary correction. Calculate the amount of nitrogen according to the following equation.

$$\text{Amount (\%) of nitrogen} = \frac{(A-B)\times 70.03}{\text{amount (g) of sample}\times(100-C)}$$

A: Volume (ml) of 0.0025 N potassium polyvinyl sulfate used for determination.

B: Volume (ml) of 0.0025 N potassium polyvinyl sulfate used for blank determination;

$$C = \frac{\text{residue on ignition (\%)}}{\text{residue on drying (\%)}}\times 1000\times 0.8229$$

0.8229:coefficient of residue on ignition (sodium sulfate expressed in sodium chloride)

(2) Degree of substitution by quaternary nitrogen-containing group

When the average number of moles of the substituent is represented by y, the molecular weight of the glucose unit of the hydroxyethylcellulose employed as the starting material is expressed in (162+44y). The molecular weight of glycidyltrimethylammonium chloride employed as the cationizing agent is 151.5. Thus, the relation between the nitrogen content N (%) and the cationization degree-can be expressed by the following formula:

Nitrogen content N (%)=[14x/(m.w. of glucose unit of cationized hydroxyalkylcellulose)]×100=[14x/m.w. of starting hydroxyalkylcellulose)+151.5x)]×100=[14x/(162+44y +151.5x)]×100.

Therefore, the degree of cationization (degree of substitution by the quaternary nitrogen-containing group) can be determined in accordance with the following formula:

Degree of cationization (x)[Nx(162+44y)]/[1400−151.5N].

(3) Mobility distribution (AU)

Electrophoresis was effected under the conditions as will be specified below by using an electrophoretic apparatus (Tsukasa Tiselius Model HBT-2A; manufactured by Tsukasa Kogyo Inc.) with the use of the Schlieren optical system. Then the mobility U was calculated in accordance with the following formula:

(Electrophoresis conditions)

temperature: 25±0.1° C.

sample concentration: 0.2 g/100 ml solvent: 0.1 N aqueous NaCl soln.

migration current: 2 mA.

(Mobility U)

U=[(K·A)/i]×[h/t]

K: [electric conductance] *specific conductivity* of solvent [$(1.067\times10^{-2}\Omega^{-1})$] ($1.067\times10^{-2}\Omega^{-1}/cm$)

A: [sectional] *cross-sectional* area of cell (0.308 $cm^2$)

i: migration current (0.002 A)

h: migration, distance (cm)

t: migration time (sec).

FIG. 1 shows a typical example of the conditions at the interface during the electrophoresis (namely, change in refractive index (Δn) and mobility (U) at a certain point in migration time, t1). As FIG. 1 shows, the maximum mobility A, the minimum mobility B and the median mobility C for each migration time can be obtained by monitoring the changes in refractive index (Δn). As the ascending interface migrated, the points A, B and C also migrated with the passage of time. Thus, the migration distance (h) (i.e., the migration distance of each of A, B and C in the migration time (t) from the starting point) of each of A, B and C in an appropriate time (t) (the time from the starting to the measuring) was measured and thus the mobility U of each point was determined In accordance with the above formula. Then the mobilities (the values of points A, B and C) were plotted by representing the reciprocal of the migration time (1/t) on the abscissa. Thus, the relation between the mobility (U) and time (1/t) was obtained as shown in FIG. 2. By extending the time unlimitedly in FIG. 2, the mobilities ($U'_A$, $U'_B$ and $U'_C$) were determined and the mobility distribution (ΔU) was determined in accordance with, one following formula.

Mobility distribution (ΔU)=$U'_A$=$U_B$ (4) Turbidity

Solutions of PHASE I and PHASE II as will be specified below were prepared sad nixed together to give a completely homogeneous mixture. Then the turbidity of the resultant solution was measured.

TABLE 1

| | Component | Content (g) | Content (%) |
|---|---|---|---|
| PHASE I | ES | 15.45 | 30.89 |
| | AG | 1.73 | 3.46 |
| | Water | 13.78 | 27.55 |
| PHASE II | Cationized HEC | 0.48 | 0.96 |
| | NaCl | 0.69 | 1.38 |
| | Water | 17.88 | 35.76 |
| Total | | 50.01 | 100.00 |

cationized HEC: cationized hydroxyethylcellulose.
ES: sodium polyoxyethylene laurylsulfate (EMAL ™-E27C, purity: 26.4%).
AG: polyoxyethylene glycol ether methylglycoside (GLUCAM ™ E-20).

The turbidity was measured by using a turbidimeter with integrating sphere and determined in accordance with the following formula:

$$\text{Turbidity (\%)} = \frac{\text{scattered light}}{\text{total transmitted light}}\times 100$$

Examples 2 to 4, Comparative Examples 1 to 3

Cationized hydroxyethylcellulose samples were obtained by the same procedure as the one of Example 1 under the conditions as listed in Table 2. These cationized hydroxyethylcellulose samples were subjected to the same measurements as those described in Example 1. Table 2 summarizes the results.

[TABLE 2

| | Example | | | | Comp. Example | | |
|---|---|---|---|---|---|---|---|
| | 1 | 2 | 3 | 4 | 1 | 2 | 3 |
| Solvent | IPA | IPA | t-BA | t-BA | t-BA | t-BA | t-BA |
| Solvent conc. (wt. %) | 89 | 89 | 81 | 76 | 89 | 86 | 89 |
| Cationizing agent employed (g) | 100 | 100 | 61 | 65 | 59 | 59 | 60 |
| Yield (g) of final product | 175 | 170 | 177 | 177 | 170 | 175 | 175 |
| Nitrogen Content (%) | 1.9 | 1.7 | 2.0 | 2.0 | 1.7 | 1.9 | 1.9 |
| Degree of substitution by quaternary nitrogen-containing group | 0.44 | 0.39 | 0.47 | 0.47 | 0.39 | 0.44 | 0.44 |
| Viscosity (mPa · s) of 2% aq. Solution (30 rpm) | 410 | 450 | 400 | 405 | 450 | 410 | 420 |
| $\Delta U$ ($\times 10^{-5}$ $cm^2/sec \cdot V$) | 1.34 | 1.25 | 1.15 | 0.70 | 2.53 | 2.10 | 2.17 |
| Turbidity (%) | 4 | 3 | 29 | 7 | 94 | 74 | 94 |

IPA: isopropyl alcohol.
t-BA: t-butyl alcohol.]

*TABLE 2*

| | *Example* | | | | *Comp. Example* | | |
|---|---|---|---|---|---|---|---|
| | *1* | *2* | *3* | *4* | *1* | *2* | *3* |
| *Solvent* | *IPA* | *IPA* | *t-BA* | *t-BA* | *t-BA* | *t-BA* | *t-BA* |
| *Solvent conc. (wt. %)* | *89* | *89* | *81* | *76* | *89* | *86* | *89* |
| *Cationizing agent employed (g)* | *100* | *100* | *61* | *65* | *59* | *59* | *60* |
| *Yield (g) of final product* | *175* | *170* | *177* | *177* | *170* | *175* | *175* |
| *Nitrogen Content (%)* | *1.9* | *1.7* | *2.0* | *2.0* | *1.7* | *1.9* | *1.9* |
| *Degree of substitution by quaternary nitrogen-containing group* | *0.44* | *0.39* | *0.47* | *0.47* | *0.39* | *0.44* | *0.44* |
| *Viscosity (mPa · s) of 2% aq. Solution (30 rpm)* | *410* | *450* | *400* | *405* | *450* | *410* | *420* |
| *$\Delta U$ ($10^{-5}$ $cm^2/sec \cdot V$)* | *1.34* | *1.25* | *1.15* | *0.70* | *2.53* | *2.10* | *2.17* |
| *Turbidity (%)* | *4* | *3* | *29* | *7* | *94* | *74* | *94* |

*IPA: isopropyl alcohol.*
*t-BA: t-butyl alcohol.*

What is claimed is:

1. A cationized hydroxyalkylcellulose having a glucose unit represented by the following formula (I):

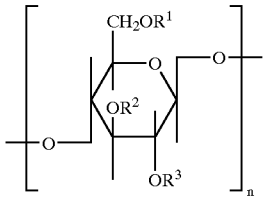

(I)

wherein $R^1$, $R^2$ and $R^3$ represent each hydrogen atom, a group represented by the following formula (II):

$$-[CH_2-\underset{\underset{R^4}{|}}{CH}-O]_a-H \qquad \text{(II)}$$

wherein $R^4$ represents hydrogen atom or methyl; and "a" is a number of from 1 to 6 on the average, or a group represented by the following formula (III):

(III)

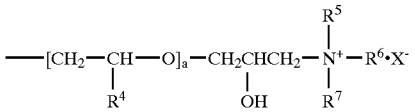

wherein $R^4$ represents hydrogen atom or methyl; "a" is a number of from 1 to 6 on the average; $R^5R^6$ and $R^7$ are the same as or different from each other and represent a methyl or ethyl; and X represents a halogen; and "n" is a number of from 50 to 2,000, the cationized hydroxyalkyl cellulose having a mobility distribution (ΔU), determined by electrophoresis, in the range of from $0.1\times[10^5]10^{-5}$ to $2.0\times[10^5]10^{-5}$ $cm^2/sec\cdot V$, including the above shown group (III) to have a nitrogen atom content (%) of from 0.1 to 10.0.

2. The cationized hydroxyalkylcellulose as set forth in claim 1, which has the substituent represented by the formula (II) at an average degree of substitution per glucose unit ranging from 0.4 to 2.9 and at an average mole number ranging from 1.0 to 7.0.

3. The cationized hydroxyalkylcellulose as set forth in claim 1, which has the substituent represented by the formula (II) at an average degree of substitution per glucose unit ranging from 0.7 to 2.1 and at an average mole number ranging from 1.6 to 3.6.

4. The cationized hydroxyalkylcellulose as set forth in claim 1, which has the substituent represented by the formula (III) at an average degree of substitution per glucose unit ranging from 0.1 to 3.0.

5. The cationized hydroxyalkylcellulose as, set forth in claim 1, which has the substituent represented by the formula (III) at an average degree of substitution per glucose unit ranging from 0.1 to 1.5.

6. The cationized hydroxyalkylcellulose as set forth in claim 1, which has the substituent represented by the formula (III) at an average degree of substitution per glucose unit ranging from 0.1 to 0.9.

7. A process for producing a cationized hydroxyalkylcellulose, comprising by the steps of mixing a hydroxyalkylcellulose with an aqueous solution of isopropyl alcohol having an isopropyl alcohol concentration of from 80 to 90 wt. % or an aqueous solution of t-butyl alcohol having a t-butyl alcohol concentration of from 75 to 85 wt. %; adding an alkali to the mixture; effecting cationization; and effecting: neutralization

* * * * *